United States Patent [19]

Winyall et al.

[11] 4,180,566
[45] Dec. 25, 1979

[54] SILICA GEL METHOD OF REDUCING BLOOD LIPID CONCENTRATION

[75] Inventors: Milton E. Winyall; Kamal M. Abdo, both of Columbia, Md.

[73] Assignee: W. R. Grace & Co., New York, N.Y.

[21] Appl. No.: 906,284

[22] Filed: May 15, 1978

[51] Int. Cl.² ............................................. A61K 33/00
[52] U.S. Cl. .................................... 424/127; 424/157; 424/357
[58] Field of Search ......................... 424/127, 157, 357

[56] References Cited
U.S. PATENT DOCUMENTS

| 4,041,153 | 8/1977 | Howard | 424/131 |
| 4,064,234 | 12/1977 | Howard | 424/157 |

OTHER PUBLICATIONS

Iler, The Colloid Chemistry of Silica & Silicates, Cornell U. Press Ithaca, NY 1955 pp. 293-299.
Patterson, The Story of Silica Gel, The Silica Gel Corp., 1930, pp. 47-48.
Szabo Chem. Abs., vol. 56, 1962, pp. 3772 g.
Stalder, Chem. Abs., vol. 74, 1971 Ab. No. 138850 m.

Primary Examiner—Anna P. Fagelson
Attorney, Agent, or Firm—Mark T. Collins

[57] ABSTRACT

A method of reducing the lipid concentration in the blood of a patient comprises administering to the patient a lipid-lowering effective amount of silica gel.

11 Claims, No Drawings

SILICA GEL METHOD OF REDUCING BLOOD LIPID CONCENTRATION

This invention relates to a method of reducing the lipid concentration in the blood, particularly in humans.

Certain diseases, such as coronary heart disease and atherosclerosis, have been associated with the presence of too high a level of cholesterol and other lipids in blood plasma. Recently, a correlation between blood levels of certain lipoproteins and susceptibility to atherosclerosis has been found. Lipoproteins are complexes of lipids, such as cholesterol and triglycerides, and proteins and are the prime carriers of these lipids in the bloodstream. An excess of low density lipoprotein has been linked with the development of atherosclerosis and high blood levels of high density liproprotein have been correlated with low incidence of heart desease. A third lipoprotein, very low density lipoprotein, is a precursor to low density lipoprotein and it may be possible to reduce low density lipoprotein levels by lowering very low density lipoprotein levels in the blood.

Considerable effort has been directed in recent years to develop substances which reduce blood levels of cholesterol, low density lipoproteins, and/or triglycerides. Four major lipid-lowering drugs that are currently available or clofibrate, dextrothyroxine, nicotinic acid, and cholestryramine. However, these substances have undesirable side effects such as blood clots, cardiac arrhythmia, or digestive disturbances.

Cholestryramine is a cross-linked styrene polymer containing tertiary amino groups and has negatively charged terminal portions that sequester or bind bile acids produced by the liver. The sequestered bile acids can not be readsorbed into the liver where they are made but instead are forced to pass out of the intestine with the feces. Because cholesterol is a metabolic precursor of bile acids in the liver, more cholesterol must be converted into bile acids to compensate for the bile acids eliminated by the action of cholestryramine so that blood levels of cholesterol and low density lipoproteins usually drop. Although its side effects are less serious than other lipid-lowering drugs, cholestryramine and other bile acid sequestering agents are taken in bulk form and are unpalatable and difficult to digest. It has recently been reported that cholestryramine hastens the elimination of Kepone from the body and that cholestryramine therapy may also be effective in lowering dangerous levels of other materials, such as polychlorinated biphenyls, polybrominated biphenyls, Mirex, and dieldrin.

According to the method of the present invention, the lipid concentration in the blood of a patient is reduced by administering to the patient silica gel in an amount of at least about 0.2 grams per kilogram of body weight. The silica gel can be administered to patients which may be animals, mammals, chickens, rats, cats, dogs, horses, and humans. In a preferred embodiment, the present invention provides a method of reducing the concentration of cholesterol in the blood of a human patient which comprises administering to the patient a silica hydrogel containing at least about 50 weight percent water in a total daily amount of at least about 8 grams.

Silica gel is effective in reducing blood lipids, particularly cholesterol and/or triglycerides, and is free of toxicity and undesirable side effects. Silica gels have a large surface area which facilitates the absorption of various molecules and pore sizes that can be varied to allow selective entrapment within a specified molecular weight range. It is believed that the silica gel used in the method of this invention reduced cholesterol levels by adsorbing bile acids in the gastrointestinal tract and thus increasing the conversion of cholesterol into bile acids and decreasing cholesterol adsorption into the blood stream. It is also believed that silica gel administered in accordance with this invention would adsorb polyhalogenated hydrocarbon poisons in the intestine and hasten their elimination from the body. Such poisons include chlorinated derivatives of cyclopentadiene, such as Kepone, Mirex, and dieldrin, and polychlorinated and polybrominated biphenyls.

The silica gel used in the method of this invention is a synthetic amorphous silica and may be a silica hydrogel, a silica aerogel, or a silica xerogel. A variety of silica gels are commercially available and their methods of preparation are well known in the art.

A preferred type of silica gel is a silica hydrogel because of the adsorption provided by its high surface area and large pore size. It is believed that the ammonia content and pH of the hydrogel also contribute to adsorption of bile acids and thus to reduction of cholesterol. Silica hydrogel may be prepared by combining, with agitation, a solution of mineral acid, such as sulfuric acid, and a solution of an alkali metal silicate, such as sodium silicate, to form a silica sol. The sodium silicate solution commonly has an $SiO_2$ concentration of 6 to 25 percent by weight and a stoichiometric excess of acid is used to provide a sol having a pH of less than 5 and commonly of between 1 to 3. The sol is allowed to set to the hydrogel and washed to free it of electrolytes. The washed hydrogel generally has a water content of from about 60 to about 80 weight percent, as measured by loss on ignition at 1750° F. (955° C.), and may be ground to the desired particle size and dried to the desired water content by oven drying, fluid energy milling, spray drying, flash drying or some other known method. Generally, the silica hydrogels used in this invention contain at least about 50 weight percent water and preferably contain from about 50 to about 75 weight percent water, as measured by loss on ignition at 1750° F. (955° C.).

The silica gel will generally be used in this invention in the form of a finely divided powder of particles having an average particle size of less than about 20 microns with less than about 0.5 percent of the particles having a particle size above about 44 microns. The silica gel powder can be orally administered to a patient either alone or in the form of a pharmaceutical preparation or in admixture with a solid or liquid food. For example, the powder may be placed in capsules, compressed into tablets, or suspended in a pharmaceutically acceptable oil or aqueous vehicle. Since the silica gel is normally administered with meals, the most convenient method of oral administration of the silica gel is by ingestion of an admixture of the gel with a solid or liquid food.

The dosage administered to the patient is a lipid-lowering effective amount of at least about 0.2 grams per kilogram of body weight of the patient and preferably of from about 0.6 to about 1.4 grams per kilogram of body weight. The dosage is based upon the total weight of the silica gel, including the water present therein, and is the amount administered per day. In human patients, the silica gel may be administered in a total daily amount of at least 8 grams to provide the desired lipid-lowering effect and preferably is administered in a total daily amount of from about 8 to about 40 grams. Since the reduction in blood lipid concentration provided by this invention is dosage and time dependent, the therapy may be continued by the physician as necessary depending upon the nature of the patient's condition and the degree of reduction of blood lipid concentration desired. Generally, the silica gel is administered for periods of at least about 90 days and the therapy repeated as necessary to maintain the desired blood lipid concentration.

The method of this invention is illustrated by the following examples. All parts and percentages in the examples are by weight unless otherwise indicated.

EXAMPLE 1

A silica hydrosol was prepared by combining, with agitation, 1 part by volume of a 50 weight percent aqueous sulfuric acid solution and 3 parts by volume of an aqueous sodium silicate solution containing 22 percent $SiO_2$ to form a silica sol having a pH of 1.5. The sol set to a gel in 15 minutes. The resulting slurry was filtered and the gel particles washed with a solution of aqueous ammonium hydroxide at 180° F. (82° C.). The washed silica hydrogel had a total volatiles content on ignition at 1750° F. (955° C.) of 70 percent and was ground in a MikroPul ACM-10 mill to an average particle size of 7.01 microns with 10 percent of the particles below 3.89 microns in size and 10 percent larger than 24.4 microns as determined in a Microtrac particle size analyzer. The properties of the ground silica hydrogel are shown in Table 1.

Table 1

| | |
|---|---|
| Total Volatiles on ignition at 1750° F. (955° C.) | 57.24% |
| $NH_3$ (dry basis) | 0.101% |
| $Na_2O$ (dry basis) | 0.052% |
| $SO_4$ (dry basis) | 0.005% |
| pH | 8.80 |

Diets containing 0, 1, 3, and 5 percent of the silica hydrogel were fed ad libitum to groups of five one-day-old chickens for eight days. High cholesterol and cholic acid diets and the diets shown in Table 2 were used.

Table 2

| Ingredients (grams) | Diet 1 | Diet 2 | Diet 3 | Diet 4 |
|---|---|---|---|---|
| (Southern States Starter Grower Mash #318) | 1800 | 1800 | 1800 | 1800 |
| Cellulose | 200 | 180 | 100 | — |
| Silica hydrogel | — | 20 | 100 | 200 |
| | 2000 | 2000 | 2000 | 2000 |

At the end of each experiment, the feed was withdrawn overnight and the chickens sacrificed. The final weight of the chickens and feed consumption were then determined. Fecal samples were collected, oven-dried at 221° F. (105° C.), and analyzed for extractable lipids according to the method described in Association of Official Agricultural Chemists, *Official Methods of Analysis*, 9th Edition (1960). Individual blood samples were collected and analyzed for total cholesterol concentration according to the method described in Seary and Berquist, 5 *Clin. Chim. Acta.*, 192-199 (1962).

No statistically significant reduction in serum cholesterol or increase in fecal lipid concentration was obtained in the chickens fed the high cholesterol and cholic acid diets containing the silica hydrogel. Cholic acid was added to the diets to aid in the adsorption of the cholesterol. It is hypothesized that the cholic acid may have tied up the active sites of the silica hydrogel. The same high cholesterol and cholic acid diet containing 2% cholestryramine was found to produce statistically significant serum cholesterol reductions and fecal lipid concentration increases. Neither cholestryramine nor silica hydrogel improved the feed efficiency of the chickens. The poorest feed efficiency was observed in the cholestryramine-fed chickens.

The effect of the oral administration of the silica hydrogel in the diets of Table 2 on serum cholesterol and fecal lipid concentrations is shown in Table 3.

Table 3

| | Control | % Silica Gel | | |
| | | 1 | 5 | 10 |
|---|---|---|---|---|
| Serum Cholesterol (mg. %) | 200.1 ± 12.4 | 180.5 ± 8.5 | *171.0 ± 8.5 | 194.5 ± 10.1 |
| Fecal Lipids (%) | 3.02 ± 0.25 | 2.94 ± 0.17 | 2.72 ± 0.26 | 2.49 ± 0.25 |

±Standard Error of Mean
*Statistically different from control at 95% confidence level The data indicate that feeding silica hydrogel resulted in a reduction of serum cholesterol. The highest reduction of 14.2 percent was observed at the 5% level of silica hydrogel and was found to be statistically significant. Fecal lipid concentration was decreased by silica hydrogel feeding. This decrease was found to be inversely correlated with silica hydrogel level in the diets. Therefore, increasing silica hydrogel levels appears to increase fat adsorption. Silica hydrogel had no effect on weight gain and feed efficiency. A 14% increase in feed intake was observed with chickens receiving the silica hydrogel diets.

EXAMPLE 2

The time dependency of the serum cholesterol reduction and the effect of silica hydrogel on the serum cholesterol of chickens fed high fat diets were investigated in a second phase of testing using a silica hydrogel prepared in accordance with the procedure of Example 1 and having the analysis shown in Table 4.

Table 4

| | |
|---|---|
| Total Volatiles on ignition at 1750° F. (955° C.) | 55.79% |
| $NH_3$ (dry basis) | 0.016% |
| $Na_2O$ (dry basis) | 0.052% |
| $SO_4$ (dry basis) | 0.029% |
| pH | 8.94 |

Four groups of 15 one-day-old chickens were fed a normal diet and four other groups are fed a high fat diet for 28 day periods. Both diets contained 0, 1, 3 and 5 percent of the silica hydrogel. The composition of the basal normal diet is shown in Table 5 and the composition of the basal high fat diet is shown in Table 6.

Table 5
COMPOSITION OF BASAL NORMAL DIET

| Ingredient | Parts |
| --- | --- |
| Ground Corn | 70.2 |
| Soybean Meal (50%) | 10.9 |
| Dried Whey | 2.5 |
| Alfalfa Meal (17%) | 2.5 |
| Dicalcium Phosphate | 1.5 |
| Limestone | 0.5 |
| Iodized Salt | 0.5 |
| DL-Methionine | 0.2 |
| Premix* | 1.0 |
| Starch | 5.0 |

*Premix:
Vitamin A 20,000 Iu/g, 1.1 g; Vitamin $D_3$ 3,000 Iu/g, 3.5 g; Riboflavin 44 mg/g, 0.8 g; Ca-pantothenate, 0.6 g; Vitamin $B_{12}$ 53 mg/g, 1.3 g; Manganese Sulfate, 2.6 g; Choline Chloride, 0.7 g; Bacitracin 0.1 g; Sucrose, 89.3 g.

Table 6
COMPOSITION OF BASAL HIGH FAT DIET

| Ingredient | Parts |
| --- | --- |
| Lard | 25.0 |
| Alfalfa Meal (17%) | 7.2 |
| Soybean Meal (50%) | 56.1 |
| Meat & Bone Meal | 5.0 |
| Whey, Dried | 3.0 |
| Vitamin Premix* | 1.0 |
| Mineral Premix** | 2.02 |
| Ethoxyquin | 0.25 |
| Methionine | 0.2 |
| Iodized Salt | 0.25 |

*Vitamin Premix (Per 100 grams of Diet): Vitamin A, 1295 IU; Vitamin $D_3$, 264.6 IU; Vitamin E, 1.3 IU; Vitamin K, 0.26 mg; Thiamin, 0.26 mg; Riboflavin, 0.52 mg; Pantothemic Acid, 1.7 mg; Pyridoxine, 0.52 mg; Niacin, 4.4 mg; Biotin, 0.019 mg; Folic Acid, 0.159 mg; Choline Chloride, 159 mg; Vitamin $B_{12}$, 0.0013 mg; made up to 1 gram with sugar.
**Mineral Premix (Per 100 grams of Diet): Calcium Phosphate Tribasic, 1.0 g; Potassium Phosphate Dibasic, 0.595 g; Manganese Sulfate, 0.018 g; Magnesium Sulfate, 0.332 g; Ferric Ammonium Citrate, 0.062 g; Cupric Sulfate, 0.008 g; Zinc Carbonate, 0.01 g; Sodium Selenite, 2 mg; Penicillin G, 0.4 g.
NOTE:
Sodium molybdate was added to drinking water (4 mg/liter). Additional biotin was also added to drinking water (0.2 mg/liter).

In order to avoid a high mortality rate in the chickens fed high fat diets, these chickens were fed commercially available starter feed for one week prior to the commencement of feeding of the high fat diets. Controlled feeding of both diets was employed by limiting the amount of feed offered to all groups to 120 percent of that of the group consuming the least amount. Water was offered ad libitum.

At 7, 14 and 28 days of feeding, five chickens from each group were withdrawn, weighed, and sacrificed and serum samples collected and analyzed for cholesterol. Plasma samples were also collected from the chickens consuming normal diets containing silica hydrogel and were analyzed for blood cholesterol and triglycerides. The total feces produced were collected dried at 221° F. (105° C.), and analyzed for total cholesterol content according to the method described in Seary and Berquist, 5 *Clin. Chim. Acta.*, 192–199 (1962). Feed intake, weight gain and feed efficiency were also calculated.

Feeding normal diets containing the various levels of silica hydrogel appeared to have no significant effect on weight gain and feed efficiency compared to chickens fed the control diet containing no silica hydrogel. The fecal compositions of the chickens fed the normal diets of Table 5 is shown in Table 7.

Table 7
FECAL COMPOSITION OF CHICKENS FED NORMAL DIETS

| Period | Control | | | 1% Silica Gel | | |
| --- | --- | --- | --- | --- | --- | --- |
| (Days) | 0-7 | 7-14 | 14-28 | 0-7 | 7-14 | 14-28 |
| Measurement | | | | | | |
| Fecal Lipids (%) | 4.9 ± 0.6 | 3.1 ± 0.2 | 3.2 ± 0.3 | 4.6 ± 0.2 | 3.0 ± 0.1 | 2.9 ± 0.3 |
| Cholesterol (mg. %) | — | 91.8 | 218.8 | — | 86.6 | 209.3 |
| Period | 3% Silica Gel | | | 5% Silica Gel | | |
| (Days) | 0-7 | 7-14 | 14-28 | 0-7 | 7-14 | 114-28 |
| Measurement | | | | | | |
| Fecal Lipids (%) | 4.3 ± 0.3 | 2.9 ± 0.3 | 2.7 ± 0.3 | 3.9 ± 0.2 | 2.5 ± 0.3 | 2.1 ± 0.1 |
| Cholesterol (mg. %) | — | 94.3 | 256.9 | — | 111.7 | 243.9 |

±Standard Error of Mean

The data in Table 7 indicate that lipid concentration in feces decreased with time and the fecal lipid concentration of the chickens consuming the diets containing the silica hydrogel was lower than that of the controls. The data also indicate that as the level of silica hydrogel increased, lipid concentration in feces decreased and silica hydrogel feeding increased the concentration of cholesterol in feces.

Table 8 shows the blood cholesterol and triglyceride results from chickens fed the normal diets of Table 5 containing varying amounts of silica hydrogel.

Table 8
CHOLESTEROL REDUCTION IN CHICKENS FED NORMAL DIETS

| Day of Sampling | 7th | | 14th | | 28th | | | | | |
| --- | --- | --- | --- | --- | --- | --- | --- | --- | --- | --- |
| Measurement Treatment | Serum Cholesterol (mg %) | % Difference From Control | Serum Cholesterol (mg %) | % Difference From Control | Serum Cholesterol (mg %) | % Difference From Control | Plasma Cholesterol (mg %) | % Difference From Control | Plasma Triglycerides (mg %) | % Difference From Control |
| Control | 276.9 | — | 233.4 | — | 207.4 | — | 141.5 | — | 67.5 | — |
| 1% Silica Gel | 277.9 | +0.4 | 224.8 | −3.7 | 189.6 | −8.6 | 132.5 | −6.4 | 63.3 | −6.2 |
| 3% Silica Gel | 303.5 | +9.6 | 209.8* | −10.1 | 185.7* | −10.5 | 134.5 | −4.9 | 71.8 | +6.4 |

Table 8-continued

| | CHOLESTEROL REDUCTION IN CHICKENS FED NORMAL DIETS | | | | | | | | | |
|---|---|---|---|---|---|---|---|---|---|---|
| Day of Sampling | 7th | | 14th | | 28th | | | | | |
| Measurement Treatment | Serum Cholesterol (mg %) | % Difference From Control | Serum Cholesterol (mg %) | % Difference From Control | Serum Cholesterol (mg %) | % Difference From Control | Plasma Cholesterol (mg %) | % Difference From Control | Plasma Triglycerides (mg %) | % Difference From Control |
| 5% Silica Gel | 262.5 | −5.2 | 207.4* | −11.1 | 175.4* | −15.4 | 128.5 | −9.2* | 57.0 | −15.6 |

*Statistically different from control value at 95% confidence level

The data in Table 8 indicate that the 1 and 3 percent levels of silica hydrogel had no effect during the first seven days of feeding. However, as feeding continued beyond seven days, serum cholesterol concentration fell below controls and this decrease continue with time. The reduction in serum cholesterol concentration appeared to be dose and time related. The highest reduction of 15.4 percent was obtained at the 5 percent silica hydrogel level after 28 days of feeding. Reduction of serum triglyceride occurred at the 1 and 5 percent silica hydrogel levels.

Feeding the high fat diet of Table 6 containing the various levels of silica hydrogel did not influence the weight gain or feed efficiency of the chickens. As shown in Table 9, the lipids and cholesterol concentration in feces after 28 days on the high fat diet was increased with increase in silica hydrogel levels.

Table 9

| FECAL COMPOSITION OF CHICKENS FED HIGH FAT DIETS | | | | | | |
|---|---|---|---|---|---|---|
| Period | Control | | | 1% Silica Gel | | |
| (Days) | 0–7 | 7–14 | 14–28 | 0–7 | 7–14 | 14–28 |
| Measurement | | | | | | |
| Fecal Lipids (%) | 11.0 ± 1.2 | 10.5 ± 1.2 | 6.2 ± 1.4 | 9.9 ± 1.2 | 10.5 ± 0.2 | 5.6 ± 0.5 |
| Cholesterol (mg. %) | — | — | 37.8 | — | — | 34.4 |
| Period | 3% Silica Gel | | | 5% Silica Gel | | |
| (Days) | 0–7 | 7–14 | 14–28 | 0–7 | 7–14 | 14–28 |
| Measurement | | | | | | |
| Fecal Lipids (%) | 9.4 ± 0.5 | 10.4 ± 1.8 | 6.3 ± 1.0 | 9.3 ± 0.4 | 10.2 ± 1.0 | 4.9 ± 9.3 |
| Cholesterol (mg. %) | — | — | 45.1 | — | — | 46.3 |

±Standard Error of Mean

As shown in Table 10, serum cholesterol reduction in chickens fed the high fat diet containing silica hydrogel increased with time and with increase in silica hydrogel level. The highest reduction of 14.3 percent was observed for the 5 percent silica hydrogel level after 28 days.

Table 10

| CHOLESTEROL REDUCTION IN CHICKENS FED HIGH FAT DIETS | | | | | | |
|---|---|---|---|---|---|---|
| Day of Sampling | 7th | | 14th | | 28th | |
| Measurement Treatment | Serum Cholesterol (mg %) | % Difference From Control | Serum Cholesterol (mg %) | % Difference From Control | Serum Cholesterol (mg %) | % Difference From Control |
| Control | 204.4 | | 220.8 | | 222.3 | |
| 1% Silica Gel | 198.2 | −3.0 | 208.7 | −5.5 | 213.8 | −3.8 |
| 3% Silica Gel | 202.4 | −1.0 | 202.8 | −8.2 | 203.1 | −8.6 |
| 5% Silica Gel | 224.1 | +9.6 | 199.0 | −9.9 | 190.5 | −14.3 |

What is claimed is:

1. A method of reducing the lipid concentration in the blood of a patient in need of same which comprises orally administering to the patient silica gel in a lipid reducing effective amount of at least about 0.2 grams per kilogram of body weight.

2. The method of claim 1 in which the silica gel is administered in an amount of from about 0.6 to about 1.4 grams per kilogram of body weight.

3. The method of claim 1 in which the silica gel is administered in a total daily amount of at least about 8 grams.

4. The method of claim 1 in which the silica gel is administered in a total daily amount of from about 8 to about 40 grams.

5. The method of claim 1 in which the silica gel is a silica hydrogel.

6. The method of claim 5 in which the silica hydrogel contains at least about 50 weight percent water.

7. The method of claim 5 in which the silica hydrogel contains from about 55 to about 75 weight percent water.

8. A method of reducing the cholesterol concentration in the blood of a human patient in need of same which comprises orally administering to the patient a silica hydrogel containing at least about 50 weight percent water in a total daily lipid reducing effective amount of at least about 8 grams.

9. The method of claim 8 in which the silica hydrogel contains from about 50 to about 75 weight percent water and is administered in a total daily amount of from about 8 to about 40 grams.

10. The method of claim 5 in which the silica hydrogel is prepared by washing silica hydrogel particles with an aqueous ammonium hydroxide solution.

11. The method of claim 8 in which the silica hydrogel is prepared by washing silica hydrogel particles with an aqueous ammonium hydroxide solution.

* * * * *